US005641511A

United States Patent [19]
Kuhrts

[11] Patent Number: 5,641,511
[45] Date of Patent: *Jun. 24, 1997

[54] GRANULAR DRUG DELIVERY SYSTEM

[75] Inventor: Eric H. Kuhrts, Santa Barbara, Calif.

[73] Assignee: Cibus Pharmaceutical, Burlingame, Calif.

[*] Notice: The term of this patent shall not extend beyond the expiration date of Pat. No. 5,466,469.

[21] Appl. No.: 527,828

[22] Filed: Sep. 13, 1995

Related U.S. Application Data

[63] Continuation of Ser. No. 218,840, Mar. 28, 1994, Pat. No. 5,466,469, which is a continuation of Ser. No. 891,772, Jun. 1, 1992, abandoned, which is a continuation-in-part of Ser. No. 440,656, Nov. 22, 1989, Pat. No. 5,118,510, which is a continuation-in-part of Ser. No. 212,715, Jun. 28, 1988, Pat. No. 4,965,252, and a continuation-in-part of Ser. No. 440, 728, Nov. 22, 1989, Pat. No. 5,023,245, which is a continuation-in-part of Ser. No. 119,188, Nov. 10, 1987, abandoned, Ser. No. 178,472, Apr. 7, 1988, abandoned, Ser. No. 212, 715, Jun. 28, 1988, Pat. No. 4,965,252, and Ser. No. 212, 607, Jun. 28, 1988, Pat. No. 4,911,917.

[51] Int. Cl.$^6$ .................................................. A61K 9/48
[52] U.S. Cl. ..................... 424/451; 424/43; 424/44; 424/490; 424/493; 424/494; 424/496; 424/686; 424/700; 514/777; 514/781; 514/782
[58] Field of Search .......................... 424/451, 43, 44, 424/655, 682, 686, 687, 700, 466, 490–496; 514/960, 782, 777, 779, 781

[56] References Cited

U.S. PATENT DOCUMENTS

| | | | |
|---|---|---|---|
| 2,935,408 | 5/1960 | Steinitz | 514/57 |
| 3,082,091 | 3/1963 | Smith | 426/96 |
| 3,850,838 | 11/1974 | Guckenberger | 252/363.5 |
| 4,127,645 | 11/1978 | Witzel | 424/44 |
| 4,462,982 | 7/1984 | Samejima | 424/495 |
| 4,687,662 | 8/1987 | Schobel | 424/44 |
| 4,747,881 | 5/1988 | Shaw et al. | 106/209 |
| 4,754,027 | 6/1988 | Applegren | 536/114 |
| 4,790,991 | 12/1988 | Shaw et al. | 424/441 |
| 4,818,539 | 4/1989 | Shaw et al. | 424/441 |
| 4,824,672 | 4/1989 | Day et al. | 424/195.1 |
| 4,886,669 | 12/1989 | Ventouras | 424/469 |
| 4,888,177 | 12/1989 | Gergely | 424/466 |

FOREIGN PATENT DOCUMENTS

| | | |
|---|---|---|
| 0007619 | 2/1980 | European Pat. Off. . |
| 0080673 | 4/1983 | European Pat. Off. . |
| 59175436 | 3/1983 | Japan . |
| 2021948 | 12/1979 | United Kingdom . |
| 2030583 | 4/1980 | United Kingdom . |

OTHER PUBLICATIONS

Council Report, "Dietary Fiber and Health" *Journal of the American Medical Association* 262(4):542–546 (Jul. 28, 1989).

Remington's Pharamceutical Sciences pp. 1622 and 1623 (1990).

*Primary Examiner*—D. Gabrielle Phelan
*Attorney, Agent, or Firm*—Cooley Godward LLP

[57] ABSTRACT

A novel granular drug delivery system having a gel-forming dietary fiber that can be made into a an orally-ingestible dispersion by admixture with a liquid that can deliver an effective dose of a pharmaceutically-active compound. The granular drug delivery system comprises granules consisting essentially of a pharmaceutically active compound, and a gel-forming dietary fiber, the granules being coated with at least one of the following: a gel-forming dietary fiber, a starch or a protein. The composition may further include a mineral salt that releases a physiologically-acceptable gas upon ingestion. The composition of the granular drug delivery system will deliver microgram quantities of a pharmaceutically-active compound in an orally-ingestible dispersion without forming a thick gel and without forming "hot" and "cold" spots of the pharmaceutically-active compound.

16 Claims, No Drawings

GRANULAR DRUG DELIVERY SYSTEM

CROSS REFERENCE TO RELATED APPLICATIONS

This application is a continuation of U.S. application Ser. No. 08/218,840, filed Mar. 28, 1994, now U.S. Pat. No. 5,466,469 which is a file-wrapper-continuation of U.S. application Ser. No. 07/891,772 filed Jun. 1, 1992 (now abandoned), which in turn is a continuation-in-part of Ser. No. 07/440,656, now U.S. Pat. No. 5,118,510, filed Nov. 22, 1989 and issued Jun. 2, 1993, which in turn is a continuation-in-part of (i) Ser. No. 07/212,715, now U.S. Pat. No. 4,965,252 filed Jun. 28, 1988 and issued Oct. 23, 1990 and (ii) Ser. No. 07/440,728, now U.S. Pat. No. 5,023,245, filed Nov. 22, 1989 and issued Jun. 11, 1991, which in turn is a continuation-in-part of Ser. No. 119,188, Nov. 10, 1987, abandoned, and a continuation-in-part of Ser. No. 178,472, Apr. 7, 1988, now abandoned, and a continuation-in-part of Ser. No. 212,715, Jun. 28, 1988, U.S. Pat. No. 4,965,252, and a continuation-in-part of Ser. No. 212,607, Jun. 28, 1988, U.S. Pat. No. 4,911,917.

FIELD OF THE INVENTION

The present invention relates to granular drug delivery systems and, more particularly, to granular drug delivery systems having a gel-forming dietary fiber that can be made into an orally-ingestible dispersion by admixture with a liquid.

BACKGROUND OF THE INVENTION

Many pharmaceutically-active compounds that have therapeutic values to human beings are effective only in microgram quantities or in time-released quantities. There are, however, many problems inherent in the administering of these pharmaceutically-active compounds to human beings. For instance, if the pharmaceutically-active compound is to be administered by the use of a granular or powdered drink mix, it may be difficult to distribute the microgram quantities of the compound evenly. "Hot spots," where the compound is present in larger amounts, or "cold spots," where the compound may not be present at all, are conditions which make the administering of microgram quantities of a pharmaceutically-active compound difficult. This delivery problem is particularly associated with pharmaceutically-active compounds that are potent and must be delivered in fairly large or small quantities.

The distribution of pharmaceutically-active compounds is further hindered by the fact that these compounds are commonly delivered in time-released formulations. The time-released formulations used for the delivery of these compounds usually include a gel-forming dietary fiber. One type of gel-forming dietary fiber known in the art is guar gum. Guar gum (Cyamopsis Tetragonoloba), a galactomannan polysaccharide, and other gel-forming fibers such as psyllium hydrophilic mucilloid, have been recognized for some time to have a therapeutic value for lowering cholesterol and helping to regulate blood sugar.

Although guar gum is used in the food industry for various purposes as a food additive, it presents certain problems even at fairly low levels. Unfortunately, the gel-forming dietary fibers, such as guar gum, are known to incompletely dissolve by forming an impenetrable layer of gel around an undissolved fiber core when introduced into a liquid for dissolving the fibers. This impenetrable layer prevents the pharmaceutically-active compound within the gel-forming dietary fiber from being released from the tablet or granule in which it is contained. These problems are exacerbated even further when the gel-forming dietary fiber is used in granular or powdered drink mix formulations. The gel-forming dietary fiber is not only extremely difficult to mix and dissolve, but what small amount does hydrate immediately may form a thick gel which becomes impossible to drink.

Various additives normally used as disintegrants to break up tablets, such as crosslinking or wicking agents or microcrystalline cellulose, however, do not solve the problem of dispersing the gel-forming dietary fiber in a solution. It has been discovered, however, that the inclusion within the tablet or granule of a mineral salt that produces a physiologically-acceptable gas will safely and effectively disperse the gel-forming dietary fiber and will thus prevent the formation of an impenetrable gel around the tablet or granule. For instance, Day and Kuhrts (U.S. Pat. No. 4,824,672) teach the use of mineral carbonates to enhance dispersion of guar gum and other gummy fibers.

The use of a suspension agent with a gum to overcome some of the problems associated with using gums as stabilizers in the food industry have been described, however, the suspension agents form slurries which are not suitable for a pharmaceutical dosage form. For instance, Steinitz (U.S. Pat. No. 2,935,408) describes the use of a suspension agent with a gum. The gum is predispersed in a non-aqueous water-free liquid matrix, thereby to condition it for further dispersal throughout an aqueous carrier. One suspension agent used was glyceryl monosterate. A slurry was formed, which can be used as a stabilizer to be added to an aqueous solution such as a gravy, salad dressing, toppings, jams, etc. This slurry, however, is not suitable for a pharmaceutical dosage form.

Further, efforts to inhibit the viscosity of the gel-forming dietary fiber have proven futile for pharmaceutical purposes. For instance, Showa Sangyo (J.P. 59175436) discloses inhibiting the viscosity (gelation) of polysaccharides (e.g., guar gum, etc.), by treating the polysaccharides with high pressure or ultrasonic waves. However, this treatment could destroy the activity of the guar gum by producing a structural change, which would destroy the pharmaceutical benefits of the gel-forming dietary fibers.

Other efforts to form particles of gel-forming dietary fibers by agglomeration, although effective, have proven difficult to control. For instance, Heath (G.B. 2030583) discloses the formation of a granulate of guar by agglomeration. The agglomeration produces powder particles that will dissolve in water, producing drinkable mixtures. The granules of guar are then formed by spraying the powder with atomized water and then drying the granules to create particles of 100 to 1000 microns having a water content of 5 to 25% by weight. The problem with this process of forming guar particles is that it is very difficult to control particle growth when spraying guar with just water.

Further, the step of coating the gel-forming dietary fibers and pharmaceutically-active compound granules with a pre-swelled hydrocolloid has been described, however, these combinations suffer from the problem of incomplete dispersion or hydration. For instance, U.S. Pat. Nos. 4,790,991, 4,747,881, and 4,818,539 disclose coating dietary fibers and drugs with a pre-swelled hydrocolloid, wherein the substrate (drug or fiber) and the hydrocolloid are not the identical material, and wherein the substrate contains cholestyramine. The hydrocolloids are selected from the group consisting of natural and modified gums, cellulose, modified celluloses, pectin, mucilages, modified starches, etc. U.S. Pat. Nos. 4,747,881, in particular, discloses coating locust bean gum with carboxy methylcellulose. The particles created tend to form small spheres which have a gel coating around their circumference when they are hydrated. They hydrocolloid coating slows down the gelation of the aggregate, but each individual particle does not fully disperse or hydrate when the hydrocolloid layer dissolves and the gastric fluid comes in contact with the core material (substrate).

Others have tried using gelatin hydrolysates to inhibit the gelation of gel-forming fibers, however, this process is not useful for administering therapeutic amounts of the gel-forming dietary fiber. For instance, EPO 0007619 discloses the use of gelatin hydrolysates to inhibit the gelation of polysaccharide gums such as guar or locust bean gums. The gelation of the gum is inhibited by admixing or blending it with gelatin and adding an effective quantity of alkalinizer such as sodium glycinate. The preferred ratio of guar gum to gelatin, however, is 0.5:1, which means that there is twice as much inhibitor as guar gum. This severely limits the usefulness of that mixture, since the guar gum must be taken in large amounts to be therapeutically effective, and one would be consuming large amounts of gelatin with it. Thus, in a daily dose of 15 grams of guar gum, one would also be consuming 30 grams or more of gelatin, which is undesirable.

Others have attempted to coat the gel-forming dietary fiber with a layer of protein, however, this process produces a composition which gels slowly when mixed with water. For instance, GB 2021948 discloses the coating of gums such as guar gum or locust bean gum with a layer of protein such as soya flour, gluten, or casein having a greater tendency to absorb water than the gum. The gum and the coating substance are mixed in preferably equal amounts with water to produce a dough which is dried and crushed. The resulting composition gels slowly when mixed with water.

Accordingly, it is an object of the present invention to provide a granular drug delivery system that delivers an effective dose of a pharmaceutically-active compound when dispersed in an orally-digestible liquid.

It is a further object of the present invention to provide a granular drug delivery system including a gel-forming dietary fiber that can be readily made into an orally-ingestible dispersion by admixture with a liquid where the gel-forming dietary fiber will mix and dissolve and will not hydrate immediately to form a thick gel which is impossible to drink.

It is yet a further object of the present invention to provide a granular drug delivery system including a gel-forming dietary fiber that can be readily made into an orally-ingestible dispersion by admixture with a liquid, the composition including a mineral salt that releases a physiologically-acceptable gas when ingested to mechanically disperse the gel-forming dietary fiber.

It is yet a further object of the present invention to provide a granular drug delivery system including a gel-forming dietary fiber that can be readily made into an orally-ingestible dispersion by admixture with a liquid, the composition including a fiber, protein or starch coating on the granules to further facilitate the dispersion of the gel-forming dietary fiber and the dispersion of the pharmaceutically-active compound.

It is yet a further object of the present invention to provide a granular drug delivery system including a gel-forming dietary fiber that can be readily made into an orally-ingestible dispersion by admixture with a liquid and that delivers an effective dose of a pharmaceutically-active compound without the formation of "hot spots" or "cold spots" of the pharmaceutically-active compound.

It is yet a further object of the present invention to provide a granular drug delivery system including a gel-forming dietary fiber that can be readily made into an orally-ingestible dispersion by admixture with a liquid and that delivers an effective dose of a pharmaceutically-active compound where the pharmaceutically-active compound is provided in microgram quantities.

It is yet a further object of the present invention to provide a granular drug delivery system including a gel-forming dietary fiber that can be readily made into an orally-ingestible dispersion by admixture with a liquid and that delivers an effective dose of a pharmaceutically-active compound where the pharmaceutically-active compound is chromium, niacin, aspirin, ibuprofen, an analgesic, an antihypercholesteromeric, a vitamin, a stimulant, an appetite suppressant, an antibiotic, an antihistamine, phenylpropanolamine hydrochloride, caffeine, a decongestant, an antitussive, or a mineral supplement.

It will be appreciated from the foregoing that there is a definite need for a granular drug delivery system that provides the above objects. The present invention fulfills these needs.

SUMMARY OF THE INVENTION

In accordance with the present invention, a granular drug delivery system is provided. The granular drug delivery system of the present invention comprises a composition including a gel-forming dietary fiber that can be made into an orally-ingestible dispersion by admixture with a liquid and that can deliver an effective dose of a pharmaceutically-active compound. The composition of the present invention will deliver microgram quantities of a pharmaceutically-active compound in an orally-ingestible dispersion without forming a thick gel when hydrated and without forming "hot" and "cold" spots of the pharmaceutically-active compound. The foregoing objects are achieved through a composition that can be made into a dispersion by admixture with a liquid, the composition comprising granules having a pharmaceutically-active compound and a gel-forming dietary fiber, the granules being coated with a gel-forming dietary fiber, a starch or a protein.

In one preferred embodiment of the present invention, the gel-forming fiber is one or more of the following: guar gum, psyllium seed husks, pectin or a pectic substance, algal polysaccharides, glucomannan, cellulose, agar or lignin. The gel-forming dietary fiber preferably comprises between about 10% to 99.999% by weight of the composition. Thus, the gel-forming dietary fiber may be present in a composition to accommodate microgram quantities of a pharmaceutically-active compound.

The pharmaceutically-active compound is preferably one or more of the following: chromium, niacin, aspirin, ibuprofen, an analgesic, an antihypercholesteromeric, a vitamin, a stimulant, an appetite suppressant, an antibiotic, an antihistamine, phenylpropanolamine hydrochloride, caffeine, a decongestant, an antitussive, a protein, a nonsteroidal, anti-inflammatory agent or a mineral supplement. The pharmaceutically-active compound preferably comprises between about $5 \times 10^{-7}\%$ to about 50% by weight of the composition. Thus, the pharmaceutically-active compound may be present in microgram quantities.

In another preferred embodiment of the present invention, a mineral salt is provided in the composition. It has been found that a mineral salt may be provided to aid in the dispersion of the granules and prevent the impenetrable gel coating of the gel-forming dietary fiber from forming around an undissolved portion of the fiber. The mineral salt aids dispersion by preferably releasing a physiologically-acceptable gas upon ingestion. The mineral salt is preferably any mineral carbonate or mineral bicarbonate and is preferably calcium carbonate, magnesium carbonate, magnesium bicarbonate, sodium carbonate, sodium bicarbonate, potassium carbonate, or potassium bicarbonate. The physiologically-acceptable gas is preferably carbon dioxide. The mineral salt, when in the composition, preferably comprises between about 1% to 30% by weight of the composition.

The ingredients of the composition are preferably formed into granules by either a wet or dry standard granulation procedure. The granules are preferably coated with a gel-forming dietary fiber, a starch or a protein. The gel-forming dietary fibers that may be used as a coating are preferably guar gum, psyllium seed husks, pectin or a pectic substance, algal polysaccharides, glucomannan, cellulose, agar or lignin. The coating is preferably a combination of a carboxymethyl cellulose coating and an ethyl cellulose coating and may be a gel-forming dietary fiber that is the same as the gel-forming dietary fiber present in the granules. The coating preferably comprises between about 0.5% to about 25% by weight of the composition. The size of the granules with the coating is preferably between about 30 to about 110 mesh, preferably 50 to 70 mesh, and most preferably sized to pass a 60 mesh screen (U.S. standard).

The granular drug delivery system of the present invention is preferably administered by making the granules into an orally-ingestible dispersion. The granules are preferably made into this dispersion by the admixture of the granules with a liquid, preferably water.

The granules are mixed in water or another orally-ingestible liquid to readily disperse the granules in the liquid. Upon ingestion, the outer coating of the granules is weakened or removed by the action of the acid of the gastrointestinal tract, thereby activating and slowly dissolving the interior of the individual granules. The internally-contained mineral salt, if included in the composition, reacts with the acid of the gastrointestinal tract to release a physiologically-acceptable gas thereby mechanically dispersing the gel-forming dietary fiber in a slow and prolonged manner. The gas assists in the disintegration of the granules by penetrating and modulating the film of the gel produced from the gel-forming dietary fiber contained within the individual granules. Thus, the proper disintegration of the granules and the proper dispersion of all of the pharmaceutically-active compounds is achieved.

By providing a granular drug delivery system having a gel-forming dietary fiber, a pharmaceutically-active compound, a coating of a gel-forming fiber, a protein, or a starch, and, in one preferred embodiment, a mineral salt that releases a physiologically-acceptable gas upon ingestion, a pharmaceutically-active compound may be administered in an orally-ingestible dispersion that will not hydrate immediate to form a thick gel and will not form "hot" or "cold" spots of the pharmaceutically-active compound.

Other objects, features, and advantages of the present invention will become apparent from a consideration of the following detailed description.

DETAILED DESCRIPTION OF THE PREFERRED EMBODIMENTS

The present invention is embodied in a granular drug delivery system that will deliver microgram quantities of a pharmaceutically-active compound in an orally-ingestible dispersion without forming a thick gel when hydrated and without forming "hot" and "cold" spots of the pharmaceutically-active compound.

In the particular embodiment herein described, the granular drug delivery system comprises a composition that can be made into an orally-ingestible dispersion by admixture with a liquid. The composition preferably comprises granules consisting essentially of a pharmaceutically-active compound and a gel-forming dietary fiber. The granules are preferably coated with a gel-forming dietary fiber, a starch or a protein. In another preferred embodiment, a mineral salt that releases a physiologically-acceptable acid upon ingestion is present in the composition.

When mixed in water or other orally-ingestible liquid, the granules of the present invention are readily dispersed. Upon ingestion, the outer coating of the granules is weakened or removed by the action of the acid of the gastrointestinal tract, thereby activating and slowly dissolving the interior of the individual granules. If present, the internally-contained mineral salt mechanically disperses the fiber upon ingestion in a slow and prolonged manner by releasing a physiologically-acceptable gas as it hydrates thereby assisting in the slow disintegration of the granules while the granules are in the gastrointestinal tract. The gas assists in the disintegration of the granules by penetrating and modulating the film of the gel produced from the gel-forming dietary fiber contained within the individual granules. Thus, the proper disintegration of the granules and the proper dispersion of all of the pharmaceutically-active compounds is achieved.

The Dietary Fiber

In a preferred embodiment of the present invention, the gel-forming dietary fibers may include mucilages, plant gums, pectins or pectic substances, algal polysaccharides, glucomannan, cellulose, agar and lignin, all of which are endogenous compounds of plant materials which are resistant to digestion by enzymes in the monogastric stomach or small intestine. Chemically, nearly all of these plant materials are carbohydrates composed of repeating monosaccharide (sugar) units. Disaccharides have two sugar units, oligosaccharides three to twelve, and polysaccharides may contain a million or more. The water-soluble fractions of these substances form gels in the stomach and intestinal tract and are known to lower serum cholesterol.

For purposes of definition in this specification, the term "dietary fiber" is defined as "remnants of plant cells resistant to hydrolysis by the alimentary enzymes of man, the group of substances that remain in the ileum but are partly hydrolyzed by bacteria in the colon", according to JAMA 262, No. 4, 542–546 (Jul. 28, 1989) in the Council Report entitled "Dietary Fiber and Health", at page 542. This article, moreover, gives considerable information as to what constitutes a "dietary fiber" and is accordingly incorporated herein by reference.

Gums and mucilages have no common structure but are polysaccharides containing several sugars with alternating monomer structures and may or may not contain uranic acids. There are many gums found in plants and cereal grains. Guar and locust bean gums are galactomannens, whereas gum arabic is an acidic polymer of galactose and rhamnose. Oat and barley contain gums, but are not practical for use in the present application because of the low percentage of active gum per weight volume. Most of the gums in the present application are effective at much lower dosages. In a preferred embodiment of the present invention, the gel-forming dietary fiber may be a gum as described above and may include, inter alia, besides guar gum, the following: locust bean gum, acacia gum, gum arabic, xanthan gum, carrageenan gum, karaya gum, tragacanth gum, and ghatti gum.

In another preferred embodiment of the present invention, the gel-forming dietary fiber may be a pectic substance or pectin. Pectins are mixtures of polysaccharides of partially methylated and 1,4-D galacturonic acid units with side chains containing arabinose, galactose, xylose, and rhamnose. They are contained in many fruits and vegetables as well as other plants.

In yet another preferred embodiment of the present invention, other gel-forming dietary fibers may be utilized, which include, but are not limited to, psyllium seed husks in powdered form, algal polysaccharides, glucomannan, cellulose, agar, and lignin. Lignin is a non-carbohydrate polymer of aromatic plant alcohols comprising oxygenated phenylpropane units. As a plant matures, more lignin is produced, which acts as a sort of cement as it hardens and holds together other plant cell wall constituents. Lignin passes through the digestive tract with very little change.

Thus, according to the invention, any of the foregoing enumerated gel-forming dietary fibers may be employed, with gums such as guar gum and the like and psyllium seed husks in powdered form being preferred, but pectin or a pectic substance, algal polysaccharides, glucomannan, agar, lignin, or the like, or combinations thereof, may generally be employed with essentially the same results.

The Mineral Salt

According to one embodiment of the present invention, any mineral salt which releases a physiologically-acceptable gas upon ingestion may be employed, although the mineral salt is not a necessary ingredient of the present invention. Such gas released is preferably carbon dioxide and the mineral salt is preferably a mineral carbonate or bicarbonate, with calcium carbonate, magnesium carbonate, magnesium bicarbonate, sodium carbonate, and sodium bicarbonate, as well as the corresponding potassium carbonate and bicarbonate, being preferred.

The Coating

The granules are preferably coated with a gel-forming dietary fiber, a starch or a protein. The gel-forming dietary fibers that may be used as a coating are preferably guar gum, psyllium seed husks, pectin or a pectic substance, algal polysaccharides, glucomannan, cellulose, agar or lignin. The coating is preferably a combination of a carboxymethyl cellulose coating and an ethyl cellulose coating and may be a gel-forming dietary fiber that is the same as the gel-forming dietary fiber present in the granules. The protein or starch coatings which are also preferably employed are gelatin, casein, soy, whey, egg, and any of various starches and modified starches.

Pharmaceutically-Active Compounds

The pharmaceutically-active compound can be any type of medication or therapeutic agent that acts systematically and that can be administered orally to transmit the active therapeutic agent into the gastrointestinal tract and into the blood-stream in therapeutically-effective levels without early excessive peak concentrations, without being inactivated by physiological fluids, and without passing unchanged through the body of the patient or subject by being excreted unabsorbed.

Among the pharmaceutically-active compounds which are preferably incorporated according to the present invention, but to which it should not be limited, are the following drugs and therapeutic agents:

1. Antipyretics and analgesics such as acetaminophen, aspirin and ibuprofen;
2. Appetite suppressants such as phenylpropanolamine hydrochloride and stimulants such as caffeine;
3. Potassium, KCl, chromium or another mineral supplement;
4. Stimulants such as caffeine;
5. Antibiotics;
6. Antihypercholesterolemics, and especially niacin;
7. Antitussives, such as dextromethorphan, dextromethorphan hydrobromide, noscapine, carbetapentane citrate, and chlophedianol hydrochloride;
8. Antihistamines, such as chlorpheniramine maleate, phenindamine tartrate, pyrilamine maleate, doxylamine succinate, and phenyltoloxamine citrate;
9. Decongestants, such as phenylephrine hydrochloride, phenylpropanolamine hydrochloride, pseudoephedrine hydrochloride, and ephedrine;
10. Vitamin C;
11. Vitamin B-12;
12. Protein; or
13. Any non-steroidal, anti-inflammatory agent.

The preferred particular drugs, minerals, or vitamins for which the present delivery system is ideally suited include: Chromium, Niacin, Vitamin B-12, Potassium Chloride, Vitamin C, Aspirin, Caffeine, Phenylpropanolamine hydrochloride, Ibuprofen, Pseudoephedrine, Nitroglycerin, a protein, a non-steroidal, anti-inflammatory agent, and Gemfibrozil.

Ranges of Ingredients

In one preferred embodiment of the present invention, the range for the gel-forming dietary fiber in the granules is between about 10% to about 99.999% by weight of the composition, the range for the mineral salt, if present, is between about 1% to about 30% by weight of the composition, and the weight of the gel-forming fiber, animal or vegetable protein, or starch coating on the particles is between about 0.5% to about 25% by weight of the composition or about 1.5% to 5% by weight of the finished product.

The pharmaceutically-active compound is preferably present in an amount of between about $5 \times 10^{-7}\%$ to about 50% by weight of the composition. Pharmaceutically-active compounds, such as chromium or other mineral supplements, folic acid or vitamin B-12 are preferably provided in microgram quantities. Thus, these compounds are preferably present in an amount of 50 micrograms in a total composition which contains 1 to 15 grams of other substances such as the gel-forming dietary fiber. Thus, the minimum percentage of these pharmaceutically-active compounds, when present in microgram quantities is about $5 \times 10^{-7}\%$ by weight of the composition.

The Granulation Procedure

The granules employed according to the present invention are prepared according to standard granulation procedure, either a wet or dry procedure, as shown in the Examples infra.

When it is desired that the pharmaceutically-active compound be released relatively slowly, the pharmaceutically-active compound is preferably pulverized and the pulverized particles coated prior to formation with the other essential ingredients of the present invention into a granule. Suitable coatings for the pharmaceutically-active compound preferably include, for example, sodium carboxymethyl cellulose. If desired, the coated pharmaceutically-active compound may be coated with a second coating, the second coating being preferably a cellulose derivative such as ethylcellulose, also shown in the Examples infra. The coating is preferably applied using a fluid bed granulator or other apparatus of the type which can rapidly and conveniently form a film over the exterior surfaces of the granules.

When the particles are formed into granules according to the normal granulation procedure, taking into consideration the ingredients involved, they should be screened to provide granules having a particle size between about 30 and 100 mesh, preferably 50 to 70 mesh, and most preferably sized to pass a 60 mesh screen (U.S. standard), so that the coating thereof with the necessary exterior coating material will provide particles of suitable dimensions for rapid dispersibility in water or other orally-ingestible liquid.

The coating of the granules with the powdered gel-forming fiber, animal or vegetable protein, or starch, which is the final step in the preparation thereof, is preferably applied using a fluid bed granulator or other apparatus of the type which can rapidly and conveniently form a film over the exterior surfaces of the granules.

EXAMPLES

The following examples are given to illustrate the preferred embodiments of the present invention, but are not to be construed as limiting.

EXAMPLE 1

Niacin-Fiber Drink Mix

A niacin granulate is produced in a fluid-bed granulator (Glatt Air Techniques, Ramsey, N.J.). The niacin is sprayed with Surelease™ (Colorcon, West Point, Pa.), an ethyl cellulose preparation, to a 10% level. The resulting granulate is 90% niacin with the 10% Surelease™ coating. The granules are screened to a 60 mesh size, and are blended with the following ingredients in the same fluid-bed granulator;

| | |
|---|---|
| Guar gum | 74.35% |
| Calcium Carbonate | 10.00% |
| Citric Acid | 5.00% |
| Niacin Granulate (90%) | 6.8% |
| Orange Flavor | 3.00% |
| Aspartame | .50% |
| Beta Carotene | .35% |

The foregoing ingredients are blended thoroughly in the fluid-bed granulator with air, and are spray dried with a 10% coating of 225 bloom gelatin dispersed in water, the final percentage of the gelatin coating being between about 2% and 25% by weight, preferably 5% to 10% by weight, and in this particular case about 7.5% by weight of the finished granules. The resulting granules are again screened to a 60 mesh size.

These granules can be mixed in water or other orally-ingestible liquid at a dose of 1 teaspoon or 5 grams, to give an extremely effective antihypercholesterolemic dose of the niacin, without the guar fiber forming a gel and solidifying. Furthermore, the niacin is not immediately released in the water so that it does not directly enter into the bloodstream, thereby preventing the typical niacin side effects of cutaneous flushing, itching, and general irritation. When the instant drink mix reaches the acid environment of the stomach or, when left long enough in solution, the mineral salt releases a physiologically-acceptable gas, carbon dioxide, thereby facilitating the dissolution of the gelatin while releasing the gel-forming fiber, calcium carbonate, citric acid and niacin. The release of the niacin is further slowed down by the coating of Surelease™, so that there is a second-stage gradual release of the niacin after the fiber has been properly dispersed by the mineral carbonate.

In further preferred embodiments of the present invention, the same composition is coated with guar gum, pectin, or with sodium caseinate (10%) instead of the gelatin shown in Example 1 in the same manner and to the same extent with similar results.

Other fibers, mineral salts, and acids may obviously replace those employed in the foregoing Example. Further, the niacin may preferably also be replaced with another pharmaceutically-active compound such as aspirin, ibuprofen, Vitamin C, chromium or the like, to provide an effective dose of the selected compound for its intended physiological effect.

EXAMPLE 2

Fiber Drink Mix

Guar Gum (100 mesh) is blended in a fluid-bed granulator (Glatt Air Techniques, Ramsey, N.J.), with calcium carbonate and citric acid. The resulting blend was composed as follows:

| | |
|---|---|
| Guar Gum | 80% |
| Calcium Carbonate | 15% |
| Citric Acid powder (60–200 mesh) | 5% |

The above blend is then spray dried with a coating of guar gum at a 0.5% level dissolved in water. The resulting granules were screened to 60 mesh and, when stirred in water, dispersed well and did not immediately gel up. The calcium carbonate aided the dispersion of the guar gum once the granules began dissolving by releasing carbon dioxide when introduced to the acid environment of the stomach. Other fibers, mineral salts, and acids may obviously replace those employed in the foregoing Example. Further, a pharmaceutically-active compound such as aspirin, Vitamin C, niacin, or the like, may be added to provide an effective dose of the selected compound for its intended physiological effect.

EXAMPLE 3

Fiber Drink Mix

Guar Gum (100 mesh) is blended in a fluid-bed granulator (Glatt Air Techniques, Ramsey, N.J.) with a microgram quantity of chromium. The resulting blend was spray dried with a coating of guar gum at a 5% level dissolved in water to produce a blend composed as follows:

| | |
|---|---|
| Guar Gum | 95% |
| Guar Gum Coating | 5% |
| Chromium | 50 mcg |

The resulting granules were screened to 60 mesh and, when stirred in water, dispersed well and did not immediately gel up. The chromium was dispersed without any "hot" spots or "cold" spots. Other fibers may obviously replace those employed in the foregoing Example. Further, a pharmaceutically-active compound such as selenium or other mineral supplement, aspirin, Vitamin B-12, niacin, ibuprofen or other non-steroidal, anti-inflammatory agent or the like, may be added to provide an effective dose of the selected compound for its intended physiological effect.

EXAMPLE 4

Nutritious Drink Mix with Fiber

A nutritious drink mix was made according to the present invention. The following ingredients were added to a Glatt fluid bed granulator and blended with air:

Roche Vitamin and Mineral Premix, containing the USRDA of all vitamins and minerals (Roche Vitamins and Fine Chemicals, Nutley, N.J.), guar gum (100 mesh), calcium carbonate, citric acid, L-selenomethionine, betacarotene, and aspartame. The ingredients were measured on a weight percentage basis to yield the following dose:

Each Dose Contains

| | |
|---|---|
| Roche Vitamin and Mineral Premix | 330 mg |
| Guar Gum | 3.4 g |
| Calcium Carbonate | 200 mg |
| Citric Acid | 150 mg |
| L-Selenomethionine | 200 mcg |
| Beta Carotene | 25,000 I.U. |

The foregoing blend is then sprayed with a coating of sodium caseinate so that the sodium caseinate comprises 10% by weight of the composition. This composition is then dried and blended with orange flavor and aspartame. The granules thus have locked-in nutrition, the Roche Vitamin and Mineral Premix, which is protected from oxidation and light by the sodium caseinate fiber until the sodium caseinate coating dissolves in the stomach.

As in the previous Examples, the granules can be mixed in water without immediately dissolving and gelling. When they reach the acid environment of the stomach, the coating dissolves and the nutritional components and fiber are released and dispersed in a gradual manner by the action of the carbon dioxide released by the calcium carbonate when introduced to the acid environment of the stomach.

Other fibers, mineral salts, and acids may obviously replace those employed in the foregoing Example. Further, the Roche Vitamin and Mineral Premix may preferably be replaced with another pharmaceutically-active compound such as aspirin, ibuprofen, Vitamin C, chromium or the like, to provide an effective dose of the selected compound for its intended physiological effect.

While a particular form of the invention has been described, it will be apparent that various modifications can be made without departing from the scope of the invention. Thus, variations may be made in the gel-forming fiber employed, the mineral salt employed, the pharmaceutically-active compound employed, and the coating of the granules employed. The above may employ any of those mentioned herein in the ranges specified, as will immediately be apparent to one skilled in the art. Accordingly, it is not intended that the invention be limited by the specific embodiment disclosed and described in detail hereinabove.

I claim:

1. A granular drug delivery composition that consists of granules and said granules of said composition consist essentially of a) a pharmaceutically-active compound and b) a gel-forming dietary fiber that is guar gum, wherein each of said granules ranges in size from about 30 to 110 mesh and is coated with ethyl cellulose.

2. The composition of claim 1, wherein said pharmaceutically active compound is a non-steroidal anti-inflammatory agent.

3. The composition of claim 1, wherein the active compound is aspirin, acetaminophen or ibuprofen.

4. The composition of claim 1, wherein the active compound is aspirin.

5. A granular drug delivery composition that consists of granules and said granules of said composition consist essentially of a) a pharmaceutically-active compound present in an amount between about $5 \times 10^{-7}$ to about 50% by weight of said composition and b) guar gum present in an amount between about 10 to about 99.999% by weight of said composition, wherein each of said granules ranges in size from about 30 to 110 mesh and is coated with ethyl cellulose.

6. The composition of claim 5, wherein said pharmaceutically-active compound is a non-steroidal anti-inflammatory agent.

7. The composition of claim 5, wherein the active compound is aspirin, ibuprofen or acetaminophen.

8. The composition of claim 7, wherein the active compound is aspirin.

9. A granular drug delivery composition, that consists of granules and said granules of said composition consist essentially of a) a pharmaceutically-active compound present in an amount between about $5 \times 10^{-7}$ to about 50% by weight of said composition and b) guar gum present in an amount between about 10 to about 99.999% by weight of said composition, wherein each of said granules ranges in size from about 50 to 70 mesh and is coated with ethyl cellulose.

10. The composition of claim 9, wherein said pharmaceutically active compound is a non-steroidal anti-inflammatory agent.

11. The composition of claim 10, wherein the active compound is aspirin, ibuprofen or acetaminophen.

12. The composition of claim 11, wherein the active compound is aspirin.

13. A composition comprising granules, wherein said granules consist essentially of a pharmaceutically-active compound and a gel-forming dietary fiber that is guar gum, the granules being coated with ethyl cellulose.

14. The composition of claim 13, wherein the pharmaceutically-active compound is aspirin, ibuprofen, or acetaminophen.

15. The composition of claim 14, wherein the active compound is aspirin.

16. The composition of claim 13, wherein the active compound is a non-steroidal anti-inflammatory agent.

* * * * *